(12) United States Patent
Liang et al.

(10) Patent No.: US 10,208,078 B1
(45) Date of Patent: Feb. 19, 2019

(54) AESCULIN THIODIPROPIONIC ACID ESTER WITH ANTIOXIDANT ACTIVITY AND A METHOD OF PREPARING THE SAME

(71) Applicants: Chengyuan Liang, Xi'an (CN); Minyi Jia, Xi'an (CN); Songsong Ruan, Xi'an (CN); Jie Li, Xi'an (CN); Lei Tian, Xi'an (CN); Xinke Ju, Xi'an (CN); Han Li, Xi'an (CN); Qianqian Zhao, Xi'an (CN); Xuechuang Wang, Xi'an (CN)

(72) Inventors: Chengyuan Liang, Xi'an (CN); Minyi Jia, Xi'an (CN); Songsong Ruan, Xi'an (CN); Jie Li, Xi'an (CN); Lei Tian, Xi'an (CN); Xinke Ju, Xi'an (CN); Han Li, Xi'an (CN); Qianqian Zhao, Xi'an (CN); Xuechuang Wang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/101,414

(22) Filed: Aug. 11, 2018

(51) Int. Cl.
*C07H 17/075* (2006.01)

(52) U.S. Cl.
CPC .................................. *C07H 17/075* (2013.01)

(58) Field of Classification Search
None
See application file for complete search history.

(56) References Cited

FOREIGN PATENT DOCUMENTS

KR 101329219 B1 * 11/2013

* cited by examiner

*Primary Examiner* — Traviss C McIntosh, III
(74) *Attorney, Agent, or Firm* — SZDC Law P.C.

(57) ABSTRACT

A compound having the following formula I:

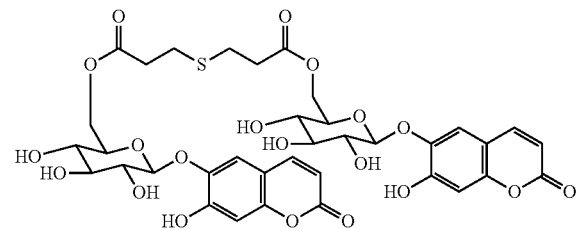

is disclosed. A method of preparing the compound of formula I is also disclosed.

10 Claims, 1 Drawing Sheet

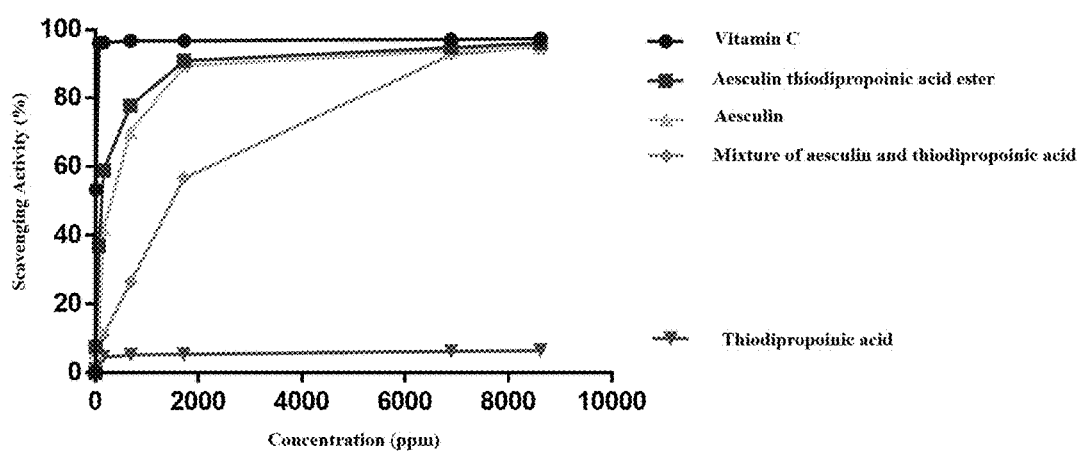

AESCULIN THIODIPROPIONIC ACID ESTER WITH ANTIOXIDANT ACTIVITY AND A METHOD OF PREPARING THE SAME

The present invention claims priority to Chinese Patent Application No. CN 201810649347.7, filed on Jun. 22, 2018, which is incorporated by reference for all purposes as if fully set forth herein.

FIELD OF THE INVENTION

The present invention relates to food and cosmetic additives, in particular, to an aesculin thiodipropionic acid ester having antioxidant activity and a method of preparing the same.

BACKGROUND OF THE INVENTION

Oxidation is the main cause of food spoilage. During storage and transportation, foods are spoiled and degraded by microorganisms. Foods also chemically react with oxygen in the air, causing them, especially oils or fats, to deteriorate. This not only reduces food nutrition, but also deteriorates flavor and color. This also produces harmful substances that endanger human health. Therefore, adding an appropriate amount of antioxidants to foods is a simple and economical method to prevent oxidative deterioration of foods.

The use of antioxidants not only prolongs the storage period and the shelf life of foods, but also brings good economic benefits to producers and distributors and gives consumers a better sense of security. At present, synthetic and semi-synthetic antioxidants have attracted more and more attentions. In addition to being used alone, the antioxidants can also be used with other food additives having other functions to form a multifunctional preparation and a dosage form, for example, packaging materials with preservatives and antioxidants.

Aesculin (compound of formula II) is coumarin compound extracted from the dry bark or dry skin of the olein tree of the genus Oleaceae, and the effective component of Chinese traditional medicine, Qinpi (Cortex Fraxini). Aesculin has anti-inflammatory, antibacterial, diuretic and anti-tumor effects. There is no report on the use of aesculin as antioxidant.

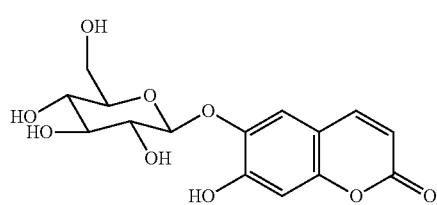

II

Thiodipropionic acid (also known as 3,3'-thiodipropionic acid; the compound of formula III) can effectively decompose the hydroperoxide in the automatic oxidation chain reaction of oil, thereby interrupting the chain reaction and improving the shelf life of oil. Thiodipropionic acid has not yet been included in China's food additive health standards (GB2760-2014), and its research on food, medicine, and health care products is lacking.

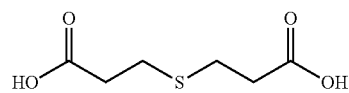

III

SUMMARY OF THE INVENTION

In one embodiment, the present invention provides a compound having the following formula I:

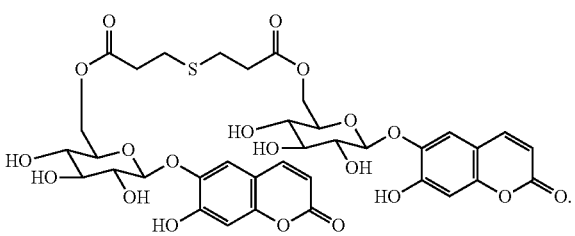

I

In one embodiment, the present invention provides a method of preparing the compound of claim 1. The method includes: reacting the compound of formula II with the compound of formula III to obtain the compound of formula I:

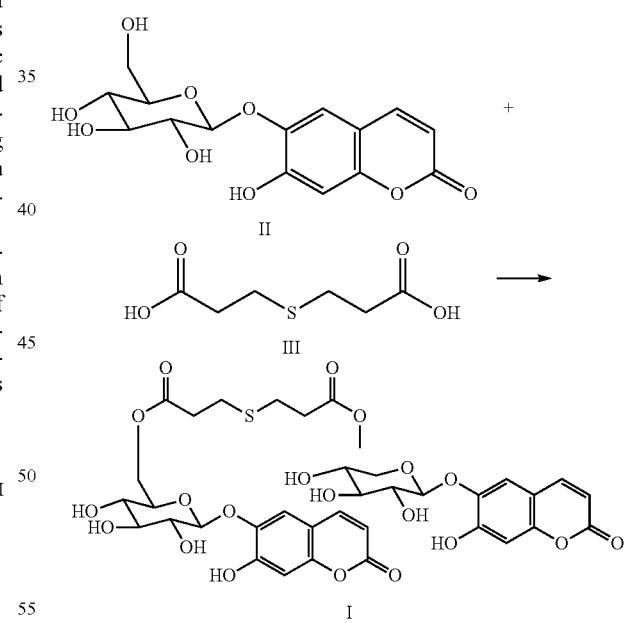

In another embodiment, the reaction of the compound of formula II with the compound of formula III comprises the following steps: placing the compound of formula II and the compound of formula III, in a molar ratio of 2:1 to 2.5:1, in a reactor; adding an organic solvent, N,N'-dicyclohexylcarbodiimide (DCC), and a catalyst to obtain a reaction mixture; and heating the reaction mixture at 30-60° C. for 4-5 hours under sonication.

In another embodiment, the organic solvent is acetonitrile or acetone.

In another embodiment, the organic solvent is acetonitrile.

In another embodiment, the catalyst is 4-dimethylaminopyridine (DMAP) or triethylamine.

In another embodiment, the catalyst is 4-dimethylaminopyridine.

In another embodiment, the molar ratio of the compound of formula II and the compound of formula III is 2.2:1.

In another embodiment, the reaction mixture is heated at 50° C.

In another embodiment, the reaction mixture is heated for 4.5 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the sample and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of the Aesculin Thiodipropionic Acid Ester (Formula I)

100 mg (0.29 mmol) aesculin and 23.8 mg (0.134 mmol) 3,3'-thiodipropionic acid were placed in a 100 mL reactor. 50 mL acetonitrile was added to form a reaction mixture. 61.9 mg (0.3 mmol) DCC and 2.6 mg DMAP were then added to the reaction mixture. The reaction mixture was heated at 40° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 107.6 mg the aesculin thiodipropionic acid ester, a yield of 89.03%.

$^1$H-NMR (400 MHz, DMSO-d6) δ (ppm): 7.67 (2H, d), 6.73 (2H, s), 6.53 (2H, s), 6.15 (2H, d), 5.86 (2H, d), 5.21 (2H, s), 4.36-4.10 (6H, m), 3.81 (2H, t), 3.52 (6H, s), 3.40-3.53 (4H, m), 2.80 (4H, t), 2.59 (4H, t); $^{13}$C-NMR (400 MHz, DMSO-d$_6$) δ (ppm): 171.6, 160.6, 148.7, 145.6, 143.0, 113.6, 111.0, 109.4, 102.7, 78.8, 76.4, 73.7, 71.5, 63.8, 34.6, 28.0; MS (ESI) for (M+H)$^+$: 823.18.

Example 2

Preparation of the Aesculin Thiodipropionic Acid Ester 100 mg (0.29 mmol) aesculin and 26.2 mg (0.147 mmol) 3,3'-thiodipropionic acid were placed in a 100 mL reactor. 50 mL acetonitrile was added to form a reaction mixture. 61.9 mg (0.3 mmol) DCC and 2.6 mg DMAP were then added to the reaction mixture. The reaction mixture was heated at 35° C. under sonication and nitrogen atmosphere for 5 hours. The reaction mixture was cooled down to room temperature, concentrated under reduced pressure, filtered, and dried with sodium sulfate. Solvent in the reaction mixture was then removed to obtain 96.8 mg the aesculin thiodipropionic acid ester, a yield of 80.12%.

Example 3

Preparation of the Aesculin Thiodipropionic Acid Ester 100 mg (0.29 mmol) aesculin and 23.8 mg (0.134 mmol) 3,3'-thiodipropionic acid were placed in a 100 mL reactor. 50 mL acetone was added to form a reaction mixture. 61.9 mg (0.3 mmol) DCC and 2.2 mg triethylamine were then added to the reaction mixture. The reaction mixture was heated at 40° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 90.1 mg the aesculin thiodipropionic acid ester, a yield of 82.01%.

Example 4

Preparation of the Aesculin Thiodipropionic Acid Ester 100 mg (0.29 mmol) aesculin and 20.9 mg (0.118 mmol) 3,3'-thiodipropionic acid were placed in a 100 mL reactor. 50 mL acetonitrile was added to form a reaction mixture. 61.9 mg (0.3 mmol) DCC and 2.2 mg triethylamine were then added to the reaction mixture. The reaction mixture was heated at 50° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 82.5 mg the aesculin thiodipropionic acid ester, a yield of 85.37%.

Example 5

Preparation of the Aesculin Thiodipropionic Acid Ester 100 mg (0.29 mmol) aesculin and 23.8 mg (0.134 mmol) 3,3'-thiodipropionic acid were placed in a 100 mL reactor. 50 mL acetone was added to form a reaction mixture. 61.9 mg (0.3 mmol) DCC and 2.6 mg DMAP were then added to the reaction mixture. The reaction mixture was heated at 45° C. under sonication and nitrogen atmosphere for 5 hours. The reaction mixture was cooled down to room temperature, concentrated under reduced pressure, filtered, and dried with sodium sulfate. Solvent in the reaction mixture was then removed to obtain 92.0 mg the aesculin thiodipropionic acid ester, a yield of 83.66%.

Example 6

The Antioxidant Activity of the Aesculin Thiodipropionic Acid Ester Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in methanol to prepare a 0.2 mmol/L DPPH solution, stored at 0° C. in dark.

Preparation of sample solutions: the aesculin thiodipropionic acid ester was diluted with a concentration gradient of 1.82, 7.28, 24.2, 48.4, 72.6, 96.8, 242, 484, 726, 968 ppm with acetonitrile to prepare sample solutions to be tested. Control samples (vitamin C, aesculin, thiodipropionic acid, a mixture of aesculin and thiodipropionic acid) were diluted with methanol in the same manner in the same concentration gradient to obtain the corresponding four groups of control solutions.

Specific Steps:

Measuring the scavenging activity of the sample solutions:

2 mL of the sample solutions at each concentration gradient was taken, 2 mL 0.2 mmol/L DPPH solution was added, the mixture was mixed and reacted at room temperature in dark for 30 minutes, and methanol was then added to adjust final volume. The absorbance $A_i$ was measured at 517 nm. 2 mL control solution and 2 mL methanol were mixed, and the absorbance $A_j$ was measured. 2 mL DPPH solution and 2 mL methanol were mixed, and the absorbance $A_0$ was measured. The scavenging activity of the sample solution and control solutions is calculated according to the following calculation formula.

$$\text{Scavenging activity }(\%) = 100 \times [1-(A_i-A_j)/A_0]$$

The scavenging activity is shown in Table 1 and FIG. 1. In FIG. 1, the X axis represents the concentrations (PPM) of the sample and control solutions, and the Y axis represents the scavenging activity.

TABLE 1

| Sample and Controls | Absorbance | Scavenging activity — Concentrations (mg/ml) | | | | | | |
|---|---|---|---|---|---|---|---|---|
| | | 6.89 | 68.9 | 172 | 689 | 1724 | 6890 | 8620 |
| Aesculin thiodipropionic acid ester | $A_i$ | 0.718 | 0.490 | 0.321 | 0.175 | 0.071 | 0.043 | 0.031 |
| | $A_j$ | 0.003 | 0.003 | 0.003 | 0.003 | 0.002 | 0.001 | 0.003 |
| | $A_0$ | | | | 0.774 | | | |
| | Scavenging activity (%) | 7.60 | 37.08 | 58.91 | 77.78 | 90.95 | 94.83 | 96.12 |
| Vitamin C | $A_i$ | 0.366 | 0.035 | 0.034 | 0.030 | 0.030 | 0.028 | 0.026 |
| | $A_j$ | 0.003 | 0.005 | 0.005 | 0.005 | 0.005 | 0.006 | 0.006 |
| | $A_0$ | | | | 0.779 | | | |
| | Scavenging activity (%) | 53.40 | 96.15 | 96.28 | 96.79 | 96.79 | 97.18 | 97.43 |
| Aesculin | $A_i$ | 0.945 | 0.873 | 0.596 | 0.279 | 0.144 | 0.094 | 0.094 |
| | $A_j$ | 0.033 | 0.031 | 0.031 | 0.034 | 0.043 | 0.052 | 0.054 |
| | $A_0$ | | | | 0.970 | | | |
| | Scavenging activity (%) | 5.98 | 13.2 | 41.75 | 70.04 | 89.58 | 93.88 | 94.80 |
| Thiodipropionic acid | $A_i$ | 0.877 | 0.851 | 0.845 | 0.840 | 0.839 | 0.831 | 0.828 |
| | $A_j$ | 0.003 | 0.001 | 0.002 | 0.002 | 0.003 | 0.003 | 0.002 |
| | $A_0$ | | | | 0.884 | | | |
| | Scavenging activity (%) | 1.13 | 3.84 | 4.64 | 5.20 | 5.43 | 6.33 | 6.57 |
| Mixture of aesculin and thiodipropionic acid (2:1) | $A_i$ | 0.919 | 0.907 | 0.869 | 0.725 | 0.438 | 0.106 | 0.090 |
| | $A_j$ | 0.023 | 0.024 | 0.024 | 0.026 | 0.027 | 0.037 | 0.045 |
| | $A_0$ | | | | 0.948 | | | |
| | Scavenging activity (%) | 5.49 | 6.86 | 10.86 | 26.27 | 56.65 | 92.72 | 95.25 |

The test results show that the antioxidant activity the aesculin thiodipropionic acid ester is similar that of vitamin C, and the free radical clearance rate of more than 90% can be achieved at a lower concentration, which is significantly higher than those of aesculin, thiodipropionic acid, and the mixture of aesculin and thiodipropionic acid. The aesculin thiodipropionic acid ester can be used a food and cosmetic antioxidant additive, and has a wide application prospect.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound having the following formula I:

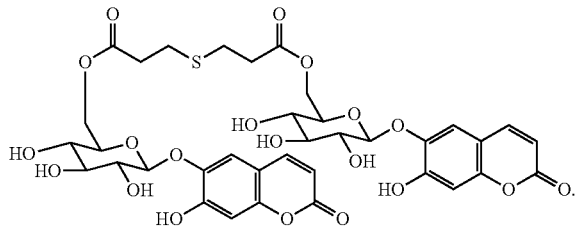 [SMILES: O=C(CCSCCC(=O)OCC1OC(Oc2cc3ccc(=O)oc3cc2O)C(O)C(O)C1O)OCC1OC(Oc2cc3ccc(=O)oc3cc2O)C(O)C(O)C1O]

2. A method of preparing the compound of claim 1, comprising:

reacting the compound of formula II with the compound of formula III to obtain the compound of formula I:

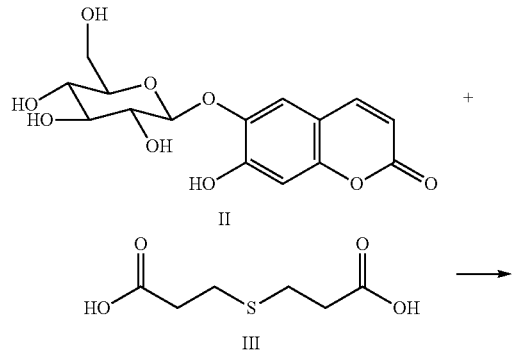

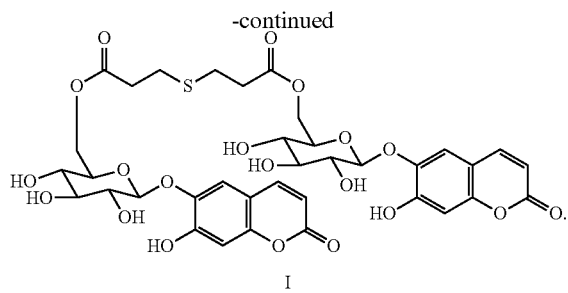

3. The method of claim 2, wherein the reaction of the compound of formula II with the compound of formula III comprises the following steps:
placing the compound of formula II and the compound of formula III, in a molar ratio of 2:1 to 2.5:1, in a reactor;
adding an organic solvent, N,N'-dicyclohexylcarbodiimide, and a catalyst to obtain a reaction mixture; and
heating the reaction mixture at 30-60° C. for 4-5 hours under sonication.

4. The method of claim 3, wherein the organic solvent is acetonitrile or acetone.

5. The method of claim 4, wherein the organic solvent is acetonitrile.

6. The method of claim 3, wherein the catalyst is 4-dimethylaminopyridine or triethylamine.

7. The method of claim 6, wherein the catalyst is 4-dimethylaminopyridine.

8. The method of claim 3, wherein the molar ratio of the compound of formula II and the compound of formula III is 2.2:1.

9. The method of claim 3, wherein the reaction mixture is heated at 50° C.

10. The method of claim 3, wherein the reaction mixture is heated for 4.5 hours.

* * * * *